(12) United States Patent
Ko et al.

(10) Patent No.: US 10,746,727 B2
(45) Date of Patent: Aug. 18, 2020

(54) USE OF LEUCINE-ZIPPER PROTEIN FOR DIAGNOSIS OR TREATMENT OF FATTY LIVER

(71) Applicant: Korea University Research and Business Foundation, Seoul (KR)

(72) Inventors: Jesang Ko, Seoul (KR); Min-Soo Kang, Goyang-si (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/466,698

(22) PCT Filed: Nov. 20, 2017

(86) PCT No.: PCT/KR2017/013154
§ 371 (c)(1),
(2) Date: Jun. 5, 2019

(87) PCT Pub. No.: WO2018/105921
PCT Pub. Date: Jun. 14, 2018

(65) Prior Publication Data
US 2019/0302101 A1    Oct. 3, 2019

(30) Foreign Application Priority Data
Dec. 7, 2016    (KR) .......................... 10-2016-0165901

(51) Int. Cl.
| | |
|---|---|
| *A61K 48/00* | (2006.01) |
| *C07H 21/04* | (2006.01) |
| *G01N 33/50* | (2006.01) |
| *A61P 1/16* | (2006.01) |
| *C12N 15/113* | (2010.01) |
| *G01N 33/68* | (2006.01) |
| *A61K 39/02* | (2006.01) |

(52) U.S. Cl.
CPC ......... *G01N 33/5023* (2013.01); *A61K 39/02* (2013.01); *A61P 1/16* (2018.01); *C12N 15/113* (2013.01); *G01N 33/6872* (2013.01); *G01N 33/6893* (2013.01); *A61K 48/00* (2013.01); *C12N 2310/11* (2013.01); *C12N 2310/122* (2013.01); *C12N 2310/14* (2013.01); *C12N 2310/531* (2013.01); *C12N 2320/31* (2013.01); *G01N 2500/04* (2013.01); *G01N 2800/085* (2013.01); *G01N 2800/7085* (2013.01)

(58) Field of Classification Search
CPC ............................. A61K 31/713; C12N 15/113
See application file for complete search history.

(56) References Cited

U.S. PATENT DOCUMENTS

2016/0074471 A1    3/2016    Ko et al.

FOREIGN PATENT DOCUMENTS

| KR | 10-2014-0129617 A | 11/2014 |
|---|---|---|
| KR | 10-1665009 B1 | 10/2016 |
| WO | 2012/051301 A1 | 4/2012 |

OTHER PUBLICATIONS

Bertrand et al. (Biochemical and Biophysical Research Communications, 296, 2002, 1000-1004).*
Yuhui Wang, et al., "Transcriptional regulation of hepatic lipogenesis", Nature, Nov. 2015, pp. 678-689, vol. 16.
NCBI, leucine zipper protein isoform, partial [*Homo sapiens*], Genbank Accession No. ACN32251.1, Jul. 24, 2016, 1 page.
Genqing Liang, "Luman/CREB3 Induces Transcription of the Endoplasmic Reticulum (ER) Stress Response Protein Herp through an ER Stress Response Element", Molecular and Cellular Biology, Nov. 2006, pp. 7999-8010, vol. 26, No. 21.
International Search Report for PCT/KR2017/013154 dated Feb. 19, 2018 [PCT/ISA/210].

* cited by examiner

*Primary Examiner* — Amy H Bowman
(74) *Attorney, Agent, or Firm* — Sughrue Mion, PLLC

(57) ABSTRACT

The present invention relates to a use of leucine-zipper protein for diagnosis or treatment of fatty liver. According to the present invention, it could be confirmed that a particular fragment present at the leucine-zipper protein, especially, the N-terminal region thereof, plays an important role in the lipid metabolism in liver tissue by regulating transcriptional activity of Apolipoprotein A4, and therefore, the protein of the present invention or a fragment thereof can be utilized as a target for diagnosis, prevention, or treatment of fatty liver.

2 Claims, 15 Drawing Sheets

Specification includes a Sequence Listing.

*F : full-size LZIP
*N : activated LZIP

FIG. 11A

| | | |
|---|---|---|
| − | + | Akt (active) |
| + | + | His-LZIP-N |
| + | + | ³²P-ATP |

LZIP

FIG. 11B

| | | |
|---|---|---|
| − | + | 10% FBS |
| + | + | BFA |
| + | + | GST-LZIP |

PD
- Akt
- GST

Input
- Akt
- GST

USE OF LEUCINE-ZIPPER PROTEIN FOR DIAGNOSIS OR TREATMENT OF FATTY LIVER

CROSS REFERENCE TO RELATED APPLICATIONS

This application is a National Stage of International Application No. PCT/KR2017/013154, filed on Nov. 20, 2017, which claims priority from Korean Patent Application No. 10-2016-0165901, filed on Dec. 7, 2016.

TECHNICAL FIELD

The present invention relates to a use of a leucine-zipper protein for diagnosis or treatment of fatty liver. The present invention was made with the support of the Ministry of Science, ICT and Future Planning of the Republic of Korea, under Project No. HI15C1906010015, and the specialized research management institution of the project is the "National Research Foundation of Korea," the research program title is the "Technology Program for Overcoming Disease," the research project title is "[⅓] A development program of metabolic disease regulation materials through studies on an associated mechanism for diabetes and diabetic vascular diseases," and the research period was "from Nov. 12, 2015, to Oct. 31, 2016."

The present patent application claims priority to and the benefit of Korean Patent Application No. 10-2016-0165901, filed on Dec. 7, 2015, the disclosure of which is incorporated herein by reference in its entirety.

BACKGROUND ART

Fatty liver is a condition where fat builds up in liver cells, and is a morbid condition where fat medically exceeds 5% or more of the total liver weight. Liver diseases including fatty liver have been reported to be among the most severe diseases after cancer among causes of death of the population of adults in their 40s to 50s in developed countries. 30% of the population of major countries including developed countries show fatty liver symptoms, 20% of these cases progress to cirrhosis, and about half of patients with cirrhosis die of liver disease within 10 years after the diagnosis.

Fatty liver may be divided into alcoholic fatty liver disease and nonalcoholic fatty liver disease (NAFLD) due to obesity, diabetes, hyperlipidemia, drugs, and the like.

Nonalcoholic fatty liver disease is simple fatty liver which does not accompany an inflammatory response from patients who do not intake excessive amounts of alcohol, and a wide range of diseases that progress therefrom including an inflammatory response of liver cells, liver fibrosis, and cirrhosis. Nonalcoholic fatty liver disease is divided into primary and secondary nonalcoholic fatty liver disease according to the cause thereof, and it is known that primary nonalcoholic fatty liver disease occurs due to hyperlipidemia, diabetes, obesity, or the like, which is a characteristic of metabolic syndromes, and secondary nonalcoholic fatty liver disease occurs due to nutritional causes (a rapid decrease in body weight, starvation, and enteric bypass), various drugs, toxic substances (poisonous mushrooms and bacterial toxins), metabolic causes, and other factors. It is known that nonalcoholic fatty liver disease is associated with diabetes and obesity which are important characteristics of metabolic syndromes which are a primary factor in about 50% of patients with diabetes, about 76% of patients with obesity, and almost of the patients with diabetes accompanying obesity. Further, as a result of performing biopsies on patients with diabetes and obesity in which the levels of alanine aminotransferase (ALT) were increased, the incidence of steatohepatitis was 18 to 36%.

Meanwhile, the therapeutic effects of administration of several diabetes or obesity therapeutic drugs on fatty liver disease are known, and there are reports that, among these therapeutic drugs, orlistat that has been used as an oral obesity therapeutic agent improves restoration of liver tissue in patients with steatohepatitis. In addition, there are reports that metformin reduces serum liver enzyme levels and necrotizing inflammation and fibrosis of the liver in patients with nonalcoholic fatty liver which does not accompany diabetes, as well as reports that a thiazolidinedione (TZD)-based drug that is an agonist of a peroxisome proliferator-activated receptor (PPAR) suppresses fat accumulation in the liver and muscles, and exhibits a direct anti-fibrosis action on the liver in animal models of nonalcoholic fatty liver disease. However, despite the development of these therapeutic drugs (Korean Patent Application Laid-Open No. 10-2013-0103190), drugs useful for the treatment of fatty liver disease are insufficient and there is no established therapeutic method for fatty liver disease, and thus the only recommendations that can be made are appropriate exercise and diet.

DISCLOSURE

Technical Problem

The present invention has been contrived to solve the aforementioned problems, and as a result of intensive studies to derive a substance which induces the synthesis of fat in the liver, the present inventors confirmed that a particular fragment present at the leucine-zipper protein, particularly, the N-terminal region thereof, promotes the accumulation of fat in liver tissue by improving the expression of Apolipoprotein A4, thereby completing the present invention based on this finding.

Thus, an object of the present invention is to provide a use of a leucine-zipper protein for prevention or treatment of fatty liver.

Thus, an object of the present invention is to provide a use of a leucine-zipper protein for diagnosis of fatty liver.

An object of the present invention is to provide a use of a leucine-zipper protein for prevention of fatty liver or development of a therapeutic medicine.

However, a technical problem to be achieved by the present invention is not limited to the aforementioned problem, and other problems that are not mentioned may be clearly understood by those skilled in the art from the following description.

Technical Solution

To achieve the aforementioned objects of the present invention, the present invention provides a pharmaceutical composition for prevention or treatment of fatty liver, including an inhibitor of expression or activity of a leucine-zipper protein as an active ingredient.

As an embodiment of the present invention, the inhibitor of expression of the leucine-zipper protein may be an antisense oligonucleotide, siRNA, or shRNA for a gene encoding the leucine-zipper protein.

As another embodiment of the present invention, the inhibitor of expression of the leucine-zipper protein may be an antibody specifically binding to the leucine-zipper protein; an antisense oligonucleotide, siRNA, or shRNA for a gene encoding a fragment consisting of an amino acid sequence of SEQ ID No. 1; and a phosphatidylinositol-3-kinase (PI3K)/Akt inhibitor.

As still another embodiment of the present invention, the composition may suppress the expression of Apolipoprotein A4.

Further, the present invention provides a composition for diagnosis of fatty liver, including a probe for measuring the expression or activity of a leucine-zipper protein.

As an embodiment of the present invention, the probe for measuring the expression of the leucine-zipper protein may be an antibody specifically binding to the leucine-zipper protein; or a nucleic acid probe or primer specifically binding to a gene encoding the leucine-zipper protein.

As another embodiment of the present invention, the probe for measuring the activity of the leucine-zipper protein may be an antibody specifically binding to a fragment consisting of an amino acid sequence of SEQ ID No. 1; or a nucleic acid probe or primer specifically binding to a gene encoding the fragment.

In addition, the present invention provides a method for screening a medicine for prevention or treatment of fatty liver, the method including: a step of culturing cells expressing a leucine-zipper protein and a candidate material in vitro and measuring the expression of the leucine-zipper protein in the cells, in which the candidate material is determined as a medicine for prevention or treatment of fatty liver when the candidate material down-regulates the expression of the leucine-zipper protein.

Furthermore, the present invention provides a method for screening a medicine for prevention or treatment of fatty liver, the method including: a step of culturing cells expressing a leucine-zipper protein and a candidate material in vitro and measuring the activity of the leucine-zipper protein in the cells, in which the candidate material is determined as a medicine for prevention or treatment of fatty liver when the candidate material down-regulates the expression of a fragment consisting of an amino acid sequence of SEQ ID No. 1.

Further, the present invention provides a method for screening a medicine for prevention or treatment of fatty liver, the method including: a step of culturing cells expressing a leucine-zipper protein and a candidate material in vitro and measuring the activity of the leucine-zipper protein in the cells, in which the candidate material is determined as a medicine for prevention or treatment of fatty liver when the candidate material reduces the formation of a complex between a fragment consisting of an amino acid sequence of SEQ ID No. 1 and Akt.

Advantageous Effects

According to the present invention, it was able to be confirmed that a particular fragment present at the leucine-zipper protein, particularly, the N-terminal region thereof, plays an important role in the lipid metabolism in liver tissue by regulating transcriptional activity of Apolipoprotein A4, and therefore, the protein of the present invention or a fragment thereof can be utilized as a target for diagnosis, prevention, or treatment of fatty liver.

DESCRIPTION OF DRAWINGS

FIG. 11A is a result of confirming whether an LZIP N-terminal binds to Akt by an in vitro kinase assay; and FIG. 11B is a result of confirming whether an LZIP N-terminal binds to Akt by a GST-pull down assay.

MODES OF THE INVENTION

Figure 1:
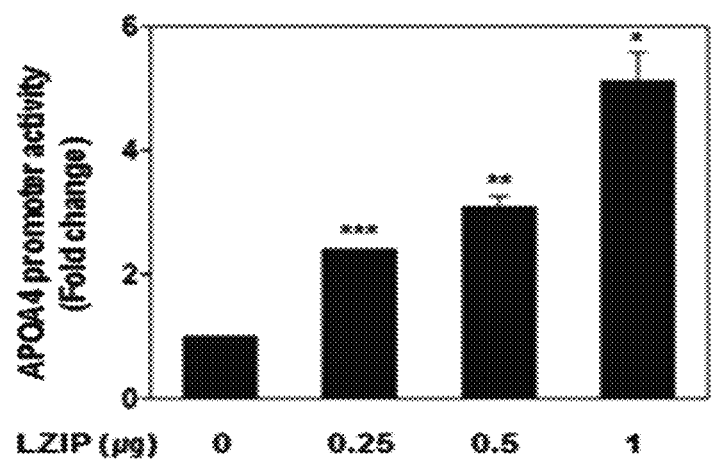
FIG. 1 is a result of measuring the activity of an ApoA4 promoter according to the concentrations (0, 0.25, 0.5, and 1 μg) in treatment with an LZIP.

Hereinafter, the present invention will be described in detail.

The present invention provides a use of a leucine-zipper protein for prevention or treatment of fatty liver.

More specifically, the present invention provides: a pharmaceutical composition for prevention or treatment of fatty liver, including an inhibitor of expression or activity of a leucine-zipper protein as an active ingredient; a use of the inhibitor of expression or activity of the leucine-zipper protein for prevention or treatment of the disease; and a method for treating the disease, the method including: a step of administering a therapeutically effective amount of the inhibitor of expression or activity of the leucine-zipper protein to an individual.

As used herein, the term "prevention" refers to all actions that suppress fatty liver disease or delay the onset of fatty liver disease by administering the pharmaceutical composition according to the present invention.

As used herein, the term "treatment" refers to all actions that ameliorate or beneficially change symptoms caused by fatty liver disease by administering the pharmaceutical composition according to the present invention.

"Fatty liver," which is the disease to be prevented or treated by the composition of the present invention, is a symptom in which fat is accumulated in an amount larger than the proportion (5%) of fat in a normal liver. Fatty liver may be largely classified into alcoholic fatty liver due to overdrinking and nonalcoholic fatty liver due to obesity, diabetes, hyperlipidemia, drugs, or the like. Alcoholic fatty liver occurs because the intake of large amounts of alcohol promotes the synthesis of fat in the liver and the normal energy metabolism is not performed, and nonalcoholic fatty liver occurs due to causes other than alcohol, and it is known that nonalcoholic fatty liver is frequently accompanied by adult diseases causing abnormalities of fat metabolism. In order to treat fatty liver disease having the symptoms described above, the present invention has a technical feature in that the present invention targets a leucine-zipper protein or a gene encoding the same, more specifically, a particular fragment in a leucine-zipper protein or a gene encoding the same.

In the present invention, the leucine-zipper protein (LZIP) belongs to the CREB/ATF gene family as a member of the bZIP family. The leucine-zipper protein has a basic DNA-binding domain and a leucine-zipper domain, and binds to a cAMP-responsive element (CRE) and an AP-1 element. In addition, the leucine-zipper was revealed as an HCF-1 binding protein that promotes the proliferation of cells and cellular transformation, and includes two LxxLL-transcription aiding factor binding motifs. Furthermore, the leucine-zipper protein consists of five members of CREB3 (LZIP, Luman), CREB3L1 (OASIS), CREB3L2 (BBF2H7), CREB3L3 (CREB-H), and CREB3L4 (AIbZIP), and these members have homology, but the respective functions of the transcription factors are different. Examples of a reported function of the leucine-zipper protein include the regulation of Lkn-1 dependent cellular movement by binding to CCR1, the regulation of expression of CCR2 by binding to a CCR2 promoter, and the like, but as disclosed in the present invention, the expression of Apolipoprotein A4 and the regulation of fat in liver tissue have not been reported.

In the present invention, an inhibitor of expression may be an antisense oligonucleotide, siRNA, shRNA, or miRNA for a gene encoding a leucine-zipper protein, or a vector including the same, and may preferably be an siRNA consisting of SEQ ID No. 5, but is not limited thereto as long as the inhibitor may exhibit an equivalent or similar effect. The antisense oligonucleotide, siRNA, shRNA, or miRNA, or the vector including the same may be constructed using a method publicly known in the art. As used herein, "vector" refers to a gene construct including an external DNA inserted into a genome encoding a polypeptide. A vector related to the present invention is a vector in which a nucleic acid sequence inhibiting the gene is inserted into a genome, and examples of the vector include a DNA vector, a plasmid vector, a cosmid vector, a bacteriophage vector, a yeast vector, or a virus vector.

Further, as used herein, an inhibitor of activity refers to a substance which allows a leucine-zipper protein to be present at a level of deterioration in function of the leucine-zipper protein, and preferably makes sensing of the function of the protein impossible or insignificant. More specifically, the inhibitor of activity may be an antibody specifically binding to the leucine-zipper protein; an antisense oligonucleotide, siRNA, shRNA, or miRNA for a gene encoding a particular fragment in the leucine-zipper protein, or a vector including the same; a substance that suppresses the activity of a particular fragment in the leucine-zipper protein, and inhibits the cleavage of an LZIP N-terminal due to Golgi stress including AEBSF, and the like, or a PI3K/Akt inhibitor including LY294002, Akt inhibitor IV, and the like, but is not limited thereto.

The particular fragment in the leucine-zipper protein is positioned at the N-terminal of the leucine-zipper protein, may consist of an amino acid sequence represented by SEQ ID No. 1, and may include an amino acid sequence having a sequence homology of 70% or more, preferably 80% or more, more preferably 90% or more, and most preferably 95% or more with the amino acid sequence represented by SEQ ID No. 1.

In addition, a gene encoding a particular fragment in the leucine-zipper protein may preferably include all types of base sequences capable of encoding an amino acid represented by SEQ ID No. 1, may most preferably consist of a base sequence represented by SEQ ID No. 2, and may include a base sequence having a sequence homology of 70% or more, preferably 80% or more, more preferably 90% or more, and most preferably 95% or more with the base sequence represented by SEQ ID No. 2.

The pharmaceutical composition of the present invention may be prepared by using an additive which is pharmaceutically suitable and physiologically acceptable in addition to an active ingredient, and a solubilizing agent such as an excipient, a disintegrant, a sweetening agent, a binder, a coating agent, an inflating agent, a lubricant, a glidant or a flavoring agent may be used as the additive.

The pharmaceutical composition of the present invention may be formulated by additionally including one or more pharmaceutically acceptable carriers in addition to an active ingredient for administration. In a composition formulated as a liquid solution, a pharmaceutically acceptable carrier may be suitable for sterilization and a living body, it is possible to use a saline solution, sterilized water, Ringer's solution, a butter saline solution, an albumin injection solution, a dextrose solution, a maltodextrin solution, glycerol, ethanol, and a mixture of at least one thereof, and other typical additives, such as an antioxidant, a buffer solution, and a bacteriostatic agent may be added, if necessary. Further, the composition may be formulated into a dosage form for injection, a pill, a capsule, a granule or a tablet, such as an aqueous solution, a suspension, and an emulsion by additionally adding a diluent, a dispersant, a surfactant, a binder, and a lubricant. Furthermore, the composition may preferably be formulated according to a specific disease or according to the ingredient by using a method disclosed in Remington's Pharmaceutical Science published by Mack Publishing Company in Easton, Pa., as an appropriate method in the corresponding art.

A pharmaceutical preparation form of the pharmaceutical composition of the present invention may be a granule, a powder, a coated tablet, a tablet, a capsule, a suppository, a syrup, a juice, a suspension, an emulsion, a drop, an injectable solution, a sustained release formulation of active compounds, or the like.

The pharmaceutical composition of the present invention may be administered in a typical method through an intravenous, intra-arterial, intraperitoneal, intramuscular, intraperitoneal, intrasternal, transdermal, intranasal, inhalation, topical, rectal, oral, intraocular, or intradermal route.

An effective amount of an active ingredient of the pharmaceutical composition of the present invention is an amount required to prevent or treat a disease or to achieve an effect of inducing bone growth. Accordingly, the effective amount of the active ingredient may be adjusted according to various factors such as a type and severity of a disease, types and contents of an active ingredient and other ingredients contained in the composition, a type of a dosage form, age, body weight, general medical conditions, sex and diet of a patient, duration and route of administration, a release rate of the composition, treatment duration, and the number of drugs simultaneously used. Although not limited thereto, for example, in the case of an adult, during administration once to several times a day, for the inhibitor of the present invention, during administration once to several times a day, administration may be performed at a dose of 0.1 ng/kg to 10 g/kg in the case of a compound, 0.1 ng/kg to 10 g/kg in the case of a polypeptide, a protein, or an antibody, and 0.01 ng/kg to 10 g/kg in the case of an antisense oligonucleotide, siRNA, shRNAi, or miRNA.

In the present invention, the 'individual' may be a human, an orangutan, a chimpanzee, a mouse, a rat, a dog, a cow, a chicken, a pig, a goat, a sheep, and the like, but is not limited to these examples.

Further, another aspect of the present invention provides a use of a leucine-zipper protein for diagnosis of fatty liver.

More specifically, the present invention provides: a composition for diagnosis of fatty liver, including a probe for measuring the expression or activity of a leucine-zipper protein; a use of the probe for measuring the expression or activity of the leucine-zipper protein for diagnosis of the disease; and a method for providing information for diagnosis of the disease, the method including a step of administering an effective amount of the probe for measuring the expression or activity of the leucine-zipper protein to an individual.

Since the composition for diagnosis of the present invention, and the like also use the above-described leucine-zipper protein, the description of content common between the two will be excluded in order to avoid excessive verbosity in the present specification.

As used herein, the term "diagnosis" refers to an action that confirms a morbid condition, that is, the presence or feature of fatty liver, by the administration of the composition according to the present invention. For the purpose of the present invention, in the diagnosis, a case where the expression or activity of the leucine-zipper protein in living tissue or a particular fragment in the leucine-zipper protein is enhanced is determined as fatty liver.

In the present invention, a probe for measuring the expression of the leucine-zipper protein may be an antibody specifically binding to the leucine-zipper protein, or a nucleic acid probe or primer specifically binding to a gene encoding the protein, a probe for measuring the activity of the leucine-zipper protein may be an antibody specifically binding to a particular fragment in the leucine-zipper protein, or a nucleic acid probe or primer specifically binding to a gene encoding the fragment, but a substance may be included without limitation as long as the substance may measure the expression or activity of the leucine-zipper protein.

As the antibody, a polyclonal antibody, a monoclonal antibody, a human antibody, and a humanized antibody, or a fragment thereof may be used. Further, the antibody fragment may include: Fab, Fab', F(ab')2 and Fv fragments; a diabody; a linear antibody; a single chain antibody molecule; and a multispecific antibody formed from antibody fragments, and the like.

The nucleic acid probe is a liner oligomer of natural or modified monomers or linkages, and is a nucleic acid probe which includes a deoxyribonucleotide and a ribonucleotide, may be specifically hybridized with a target nucleotide sequence, and is naturally present or artificially synthesized. The probe according to the present invention may be a single chain, preferably an oligodeoxyribonucleotide. The probe of the present invention may include a natural dNMP (that is, dAMP, dGMP, dCMP, and dTMP), a nucleotide analogue, or derivatives thereof. In addition, the probe of the present invention may also include a ribonucleotide. For example, the probe of the present invention may include a backbone-modified nucleotide, for example, peptide nucleic acid (PNA), phosphorothioate DNA, phosphorodithioate DNA, phosphoroamidate DNA, amide-linked DNA, MMI-linked DNA, 2'-O-methyl RNA, alpha-DNA and methyl phosphonate DNA, a sugar-modified nucleotide, for example, 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA and anhydrohexitol DNA, and a nucleotide having a base modification, for example, a C-5 substituted pyrimidine (substituents include fluoro-, bromo-, chloro-, iodo-, methyl-, ethyl-, vinyl-, formyl-, ethynyl-, propynyl-, alkynyl-, thiazolyl-, imidazolyl-, and pyridyl-), a 7-deaza-furin having a C-7 substituent (the substituent is fluoro-, bromo-, chloro-, iodo-, methyl-, ethyl-, vinyl-, formyl-, alkynyl-, alkenyl-, thiazolyl-, imidazolyl-, or pyridyl-), inosine, and diaminopurine.

The primer may be a single-stranded oligonucleotide which may act as an initiation point of template-directed DNA synthesis under suitable conditions (that is, four types of different nucleoside triphosphates and polymerases) in a suitable buffer solution at a suitable temperature. A suitable length of the primer may vary according to various factors, for example, the temperature and the use of the primer. In addition, the sequence of the primer does not need to be a sequence perfectly complementary to a partial sequence of the template, and it is enough for it to have sufficient complementarity within a range at which the primer may be hybridized with the template to exhibit the inherent function of the primer. Accordingly, the primer in the present invention does not need a sequence perfectly complementary to a nucleotide sequence of a gene which is a template, and it is enough for it to have sufficient complementarity within a range in which the primer may be hybridized with the gene sequence to act as a primer. Further, the primer according to the present invention may be used for a gene amplification reaction. The amplification reaction is a reaction in which nucleic acid molecules are amplified, and these amplification reactions of the gene are well known in the art and may include, for example, a polymerase chain reaction (PCR), a reverse transcription-polymerase chain reaction (RT-PCR), a ligase chain reaction (LCR), a transcription-mediated amplification (TMA), a nucleic acid sequence-based amplification (NASBA), and the like.

The composition for diagnosis of nonalcoholic fatty liver of the present invention may be included in the form of a kit.

The kit may include an antibody, a probe, a primer, or the like capable of measuring the activity of a leucine-zipper protein or a particular fragment in the leucine-zipper protein, and the definitions thereof may be the same as those described above.

When the kit is applied to a PCR amplification procedure, the kit may optionally include thermal stability DNA polymerases, DNA polymerase co-factors, and dNTPs obtained from a reagent required for PCR amplification, for example, a buffer solution and a DNA polymerase (for example, *Thermus aquaticus* (Taq), *Thermus thermophilus* (Tth), *Thermus filiformis*, *Thermis flavus*, *Thermococcus literalis*, or *Pyrococcus furiosus* (Pfu)), and when the kit is applied to an immunoassay, the kit of the present invention may optionally include a secondary antibody and a labeled substrate. Furthermore, the kit according to the present invention may be constructed as a plurality of separate packages or compartments including the aforementioned reagent ingredient.

Further, the composition for diagnosis of nonalcoholic fatty liver of the present invention may be included in the form of a microarray.

In the microarray of the present invention, the antibody, the probe, the primer, or the like capable of measuring the expression or activity of the leucine-zipper protein or the particular fragment in the leucine-zipper protein is used as a hybridizable array element, and is immobilized on a substrate. A preferred substrate is a suitable rigid or semi-rigid support, and examples thereof may include a membrane, a filter, a chip, a slide, a wafer, a fiber, a magnetic or non-magnetic bead, a gel, tubing, a plate, a polymer, a microparticle, and a capillary tube. The hybridizable array elements are arranged and immobilized on the substrate, and the immobilization as described above may be performed by a chemical bonding method or a covalent bonding method such as UV. For example, the hybridizable array elements may be bonded to a glass surface modified to include an epoxy compound or an aldehyde group, and further, may be bonded on a polylysine-coated surface by UV. In addition, the hybridizable array element may be bonded to a substrate through a linker (for example, an ethylene glycol oligomer and a diamine).

Meanwhile, when a sample to be applied to the microarray of the present invention is a nucleic acid, the sample may be labeled and may be hybridized with array elements on the microarray. The hybridization conditions may be diverse, and the detection and analysis of hybridization degree may be variously performed depending on the labeling materials.

As another aspect of the present invention, the present invention provides a use of a leucine-zipper protein for developing a medicine for prevention or treatment of fatty liver.

Since the screening method of the present invention, and the like also use the above-described leucine-zipper protein, the description of a content common between the two will be excluded in order to avoid excessive verbosity in the present specification.

As an embodiment, the present invention provides a method for screening a medicine for prevention or treatment of fatty liver, the method including: a step of culturing cells expressing a leucine-zipper protein and a candidate material in vitro and measuring the expression of the leucine-zipper protein in the cells, in which the candidate material is determined as a medicine for prevention or treatment of fatty liver when the candidate material down-regulates the expression of the leucine-zipper protein.

As another embodiment, the present invention provides a method for screening a medicine for prevention or treatment of fatty liver, the method including: a step of culturing cells expressing a leucine-zipper protein and a candidate material in vitro and measuring the activity of the leucine-zipper protein in the cells, in which the candidate material is determined as a medicine for prevention or treatment of fatty liver when the candidate material down-regulates the expression of the leucine-zipper protein.

As still another embodiment, the present invention provides a method for screening a medicine for prevention or treatment of fatty liver, the method including: a step of culturing cells expressing a leucine-zipper protein and a candidate material in vitro and measuring the activity of the leucine-zipper protein in the cells, in which the candidate material is determined as a medicine for prevention or treatment of fatty liver when the candidate material reduces the formation of a complex between a particular fragment in the leucine-zipper protein and Akt.

The candidate material may be the leucine-zipper protein or a material that suppresses the leucine-zipper protein from being transcribed and translated into a particular fragment by a typical selection method, or an individual nucleic acid, an individual protein, an individual peptide, another extract or natural product, compound, and the like presumed to have possibility as a medicine that suppresses the function or activity of the leucine-zipper protein or a particular fragment thereof, or randomly selected.

Thereafter, the expression level of the gene, the amount of the protein, or the activity of the protein may be measured in cells treated with the candidate material, and when the expression level of the gene, the amount of the protein, or the activity of the protein is found to be reduced as a result of measurement, the candidate material may be determined as a substance capable of preventing or treating fatty liver.

The method for measuring the expression level of a gene, the amount of a protein, or the activity of a protein may be performed by various methods publicly known in the art, and may be performed by using, for example, a reverse transcriptase-polymerase chain reaction, a real time-polymerase chain reaction, western blot, northern blot, an enzyme linked immunosorbent assay (ELISA), a radioimmunoassay (RIA), radioimmunodiffusion, an immunoprecipitation assay, and the like, but is not limited thereto.

The candidate material exhibiting the activity of inhibiting the expression of the leucine-zipper protein or a particular fragment thereof or inhibiting the function of the protein obtained by the screening method of the present invention may be a candidate material for a medicine for prevention or treatment of fatty liver.

The candidate material for the medicine for prevention or treatment of fatty liver as described above acts as a leading compound in the subsequent procedure of developing a therapeutic agent for fatty liver, and a new therapeutic agent for fatty liver may be developed by modifying and optimizing the structure of the leading compound, such that the leading compound may exhibit an effect of suppressing the function of the leucine-zipper protein or a particular fragment thereof.

Hereinafter, preferred examples for providing a clearer understanding of the present invention will be presented. However, the following examples are provided only so that the present invention can be more easily understood, and the content of the present invention is not limited by the following examples.

EXAMPLES

Example 1

Regulation of Expression of ApoA4 by Leucine-Zipper Protein

The regulation of accumulation and release of fat at the liver cell level is very important for the formation of actual fatty liver, and according to reports in the related art, it is known that fat may accumulate in tissue not only due to a high fat diet, but also due to endoplasmic reticulum stress. In view of these points, the present inventors intended to confirm the correlation between the leucine-zipper protein (hereinafter referred to as LZIP) which is one of the transcriptional factors activated by endoplasmic reticulum or Golgi stress (ER/Golgi stress) and the onset of fatty liver. Prior to this, in the present example, a change in expression of lipoprotein according to the treatment with the LZIP was confirmed, and a condition for activating the LZIP in relation with this and a specific activation site was intended to be derived.

1-1. Change in Expression of ApoA4 by LZIP in Liver Cell Line

In a liver cell line HepG2, the promoter activity of Apolipoprotein A4 (hereinafter referred to as ApoA4) caused by the concentration of treatment with the LZIP was measured, and based on the result, a change in expression level of ApoA4 mRNA and the protein caused by treatment with or suppression of the LZIP for HepG2 and Huh-7 which are liver cell lines was intended to be confirmed. In the following examples, for the treatment with or expression of the LZIP, a Flag-LZIP (pCMV-3 Tag-1 vector where an LZIP sequence in which a Flag epitope (DYKDDDDK; SEQ ID NO: 6) is tagged at the N-terminal is cloned), or an Ad-LZIP (pShuttle-IRES-hrGFP-2 vector where an LZIP sequence in which an HA epitope is tagged at the C-terminal is cloned) was used, and LZIP siRNA (SEQ ID NO: 5) was used to suppress the LZIP.

As a result, as illustrated in FIG. 1, it could be confirmed that the activity of the ApoA4 promoter was increased dependent on the concentrations (0, 0.25, 0.5, and 1 μg) in treatment with the LZIP, and as illustrated in FIGS. 2A, 2B, 3A and 3B, it was possible to observe an increase in expression of ApoA4 caused by treatment with LZIP and a decrease in expression of ApoA4 caused by suppression of LZIP in terms of both mRNA and protein levels. Meanwhile, it is known that ApoA4 is associated with alleviation of arteriosclerosis and simple transportation of fat, but there has been no report on the role in liver tissue. The change in expression of ApoA4 in liver cells by LZIP suggests the possibility of accumulation of fat in liver tissue and onset of fatty liver caused by the same.

1-2. Change in Expression of ApoA4 by Activation of LZIP According to Golgi Stress As described above, the LZIP is a transcriptional factor activated by endoplasmic reticulum or Golgi stress (ER/Golgi stress) and one of the proteins attached to the endoplasmic reticulum surface. More specifically, the present example sought to activate the LZIP by treating liver cells with brefeldin A (BFA) as a material that disassembles the Golgi apparatus, tunicamycin (TM) that suppresses the saccharification procedure in the endoplasmic reticulum, and thasigargin (TG) that depletes calcium in the endoplasmic reticulum, and then confirm the resulting change in expression of ApoA4. Meanwhile, a group treated with 1 μl of 100% methanol was used as a control (Con).

Further, when cells were treated with BFA exhibiting a significant result in the experiment, the results were verified by again confirming the activity of ApoA4 promoter, the change in expression of ApoA4 mRNA and protein, and the like, and a core mechanism for the regulation of expression of ApoA4 by the LZIP was intended to be found by observing the structural change and intracellular movement aspect of the LZIP protein by a nucleus/cytoplasm fractionation method and a fluorescence microscope. In the fluorescence analysis, the intracellular movement aspect of the LZIP protein according to the treatment with BFA was observed, and separation (degradation) of the LZIP N-terminal was intended to be confirmed by the treatment with BFA by comparing the movement aspect by the treatment with BFA with a case where cells were treated with an LZIP N-terminal (GFP tagging) which is a partially separated fragment of the LZIP. Meanwhile, a group treated with only the LZIP in which GFP is tagged was used as a control (Con).

Figure 4:
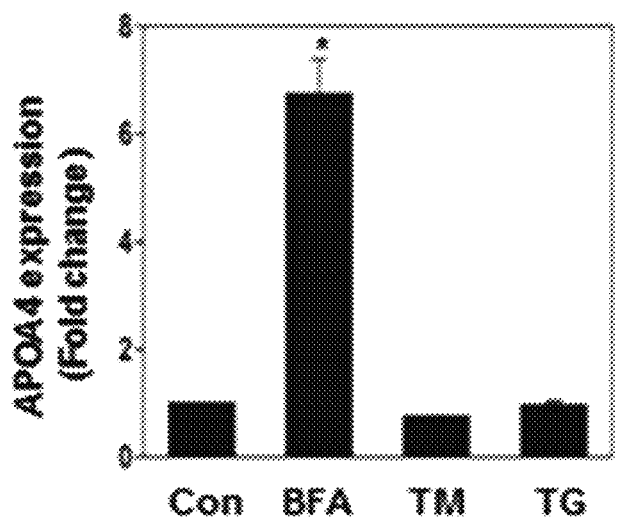
FIG. 4 is a result of confirming a change in expression of ApoA4 according to the treatment with Brefeldin A (BFA), Tunicamycin (TM), or Thasigargin (TG).
Figure 5A:
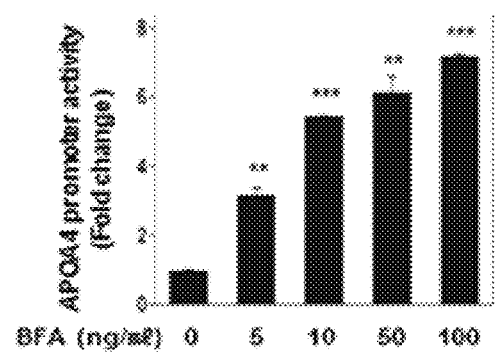
FIG. 5A is a result of measuring the activity of an ApoA4 promoter according to the concentrations (0, 5, 10, 50, and 100 ng/ml) in treatment with BFA.
Figure 5B:
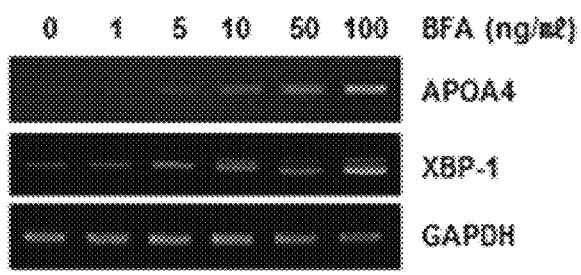
FIG. 5B is a result of confirming a change in expression level of ApoA4 mRNA according to the concentrations (0, 1, 5, 10, 50, and 100 ng/ml) in treatment with BFA.
Figure 5C:
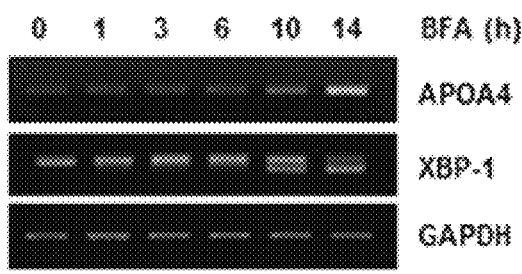
FIG. 5C is a result of confirming a change in expression level of ApoA4 mRNa according to the times (0, 1, 3, 6, 10, and 14 h) of treatment with BFA.
Figure 5D:
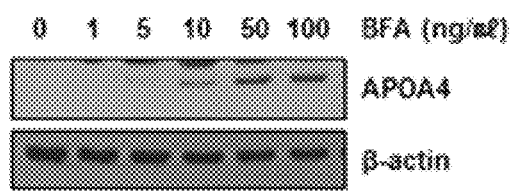
FIG. 5D is a result of confirming an expression in expression level of Apoa4 protein according to the concentrations (0, 1, 5, 10, 50, and 100 ng/ml) in treatment with BFA.

As a result, as illustrated in FIG. 4, it was able to be confirmed that when cells were treated with TM or TG, no big difference from the control was exhibited, whereas when the LZIP was activated by BFA, the expression of ApoA4 was remarkably increased. In addition, as illustrated in FIGS. 5A, 5B, 5C and 5D, it could be seen that the LZIP activated by BFA increased the activity of the ApoA4 promoter and the expression of ApoA4 mRNA and protein dependent on the concentration (5, 10, 50, and 100 ng/ml) of treated BFA or time (1, 3, 6, 10, and 14 h).

Figure 6:
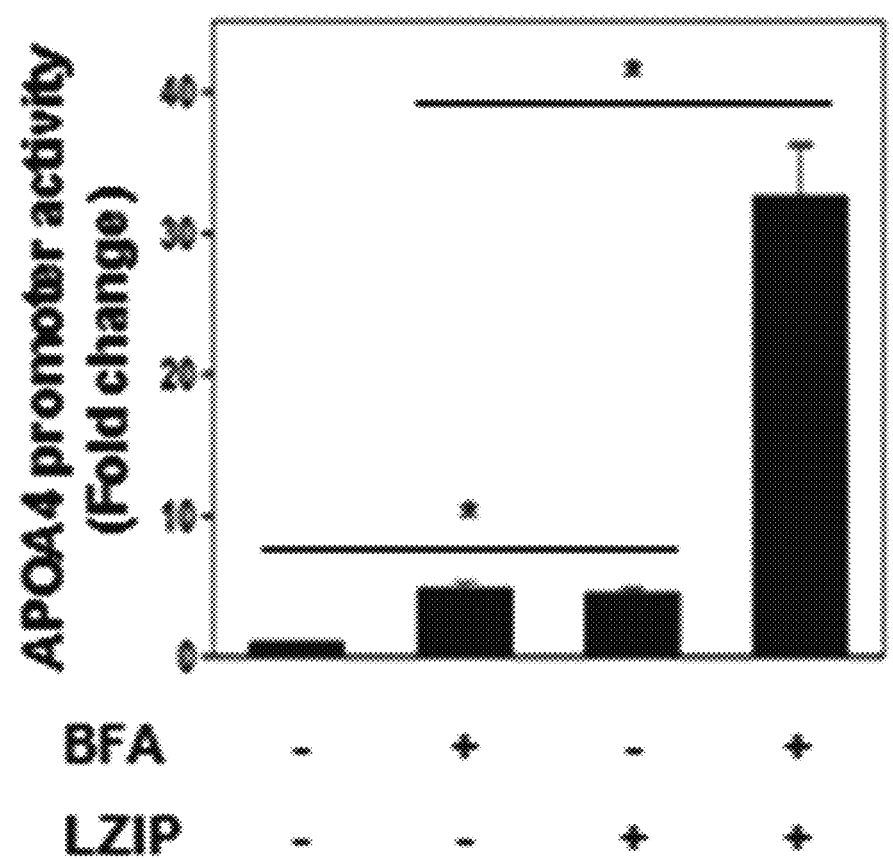
FIG. 6 is a result of measuring the activity of an ApoA4 promoter according to the combination administration of BFA and an LZIP.
Figure 7A:
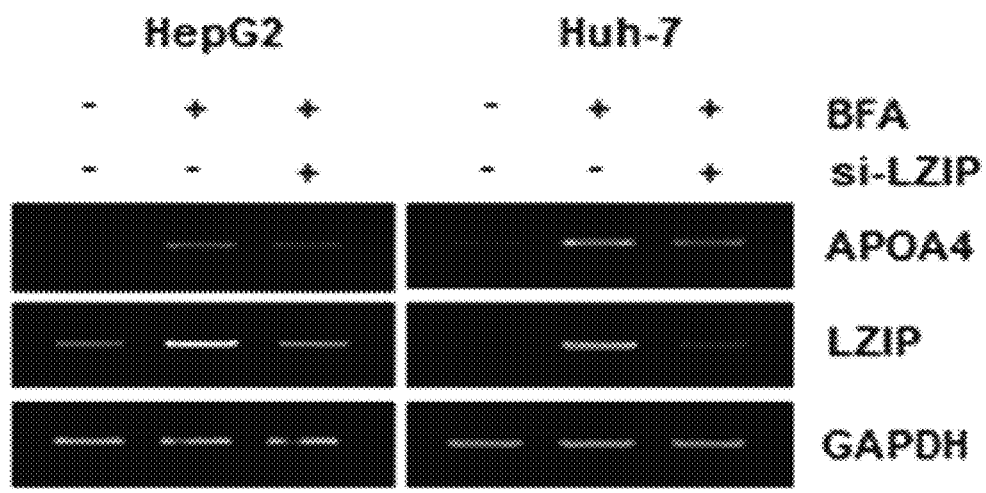
FIG. 7A is a result of confirming a change in expression level of ApoA4 mRNA according to the combination administration of BFA and LZIP siRNA.
Figure 7B:
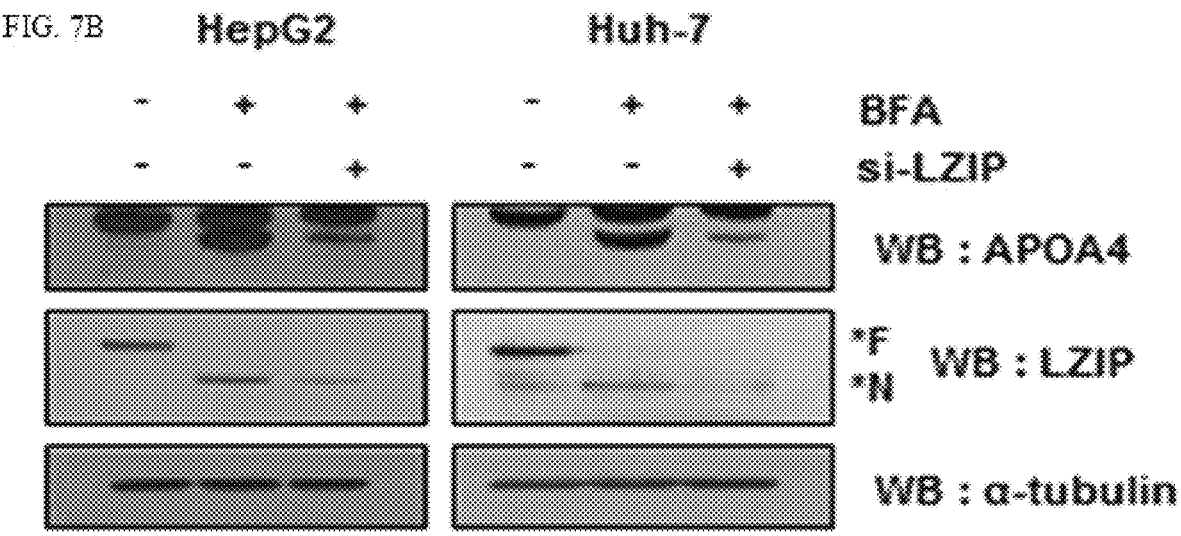
FIG. 7B is a result of confirming a change in expression level of the protein ApoA4 according to the combination administration of BFA and LZIP siRNA.
Figure 8A:
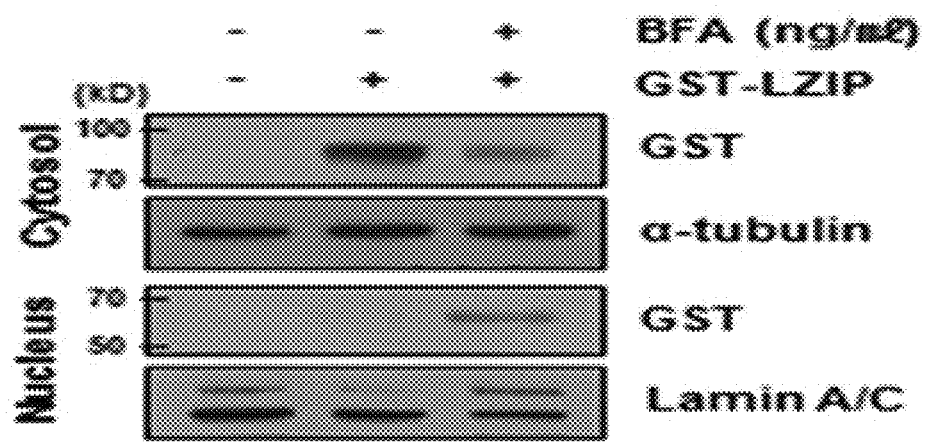
FIG. 8A is a result of confirming the intracellular movement aspect of an LZIP protein according to the treatment with BFA by a nucleus/cytoplasm fractionation method.
Figure 8B:
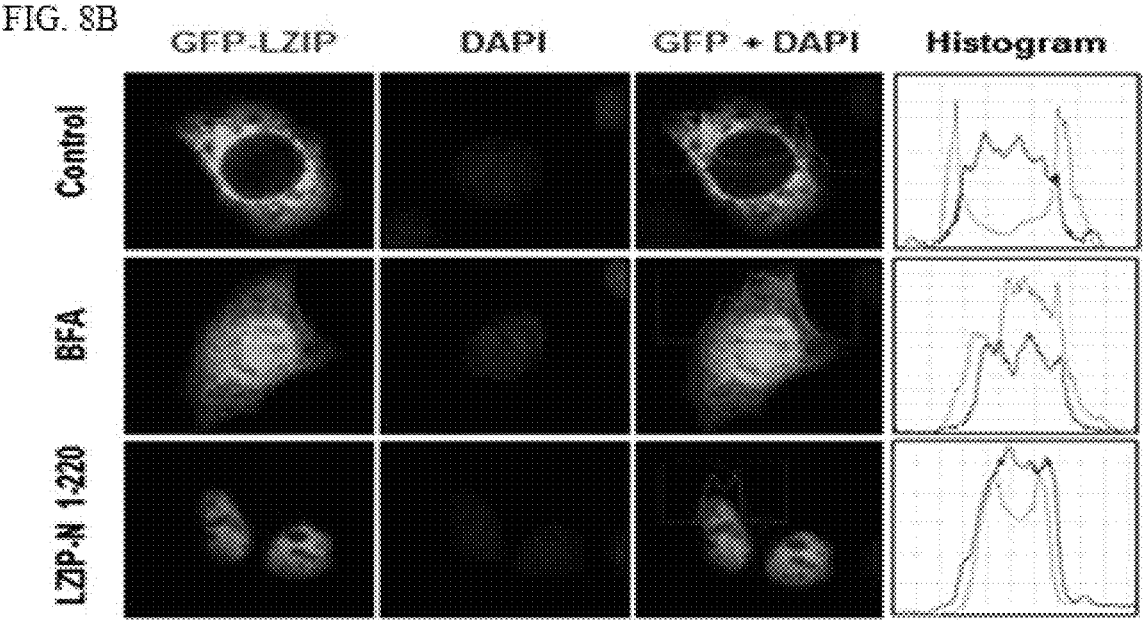
FIG. 8B is a result of observing the intracellular movement aspect of the LZIP protein according to the treatment with BFA by a fluorescence microscope.

In particular, as illustrated in FIGS. 6, 7A and 7B, the increase in expression of ApoA4 caused by the treatment with BFA was remarkable during the combination treatment with the LZIP, whereas when the expression of the LZIP was suppressed, the amount of ApoA4 mRNA and protein was decreased in both liver cells HepG2 and Huh-7, and the activation product of the LZIP, that is, the LZIP N-terminal, was also decreased, showing that the activation of the LZIP by Golgi stress played a very important role in the regulation of expression of ApoA4. Meanwhile, as a result of analyzing the movement aspect of the LZIP N-terminal by BFA, as illustrated in FIGS. 8A and 8B, it could be seen that the LZIP N-terminal was separated from the LZIP by BFA and moved from the cytoplasm to the nucleus (see FIG. 8A), and even in a fluorescence microscope analysis using GFP, when cells were treated with BFA, a larger amount of the LZIP was expressed in the nucleus than in the cytoplasm, and for the N-terminal of the GFP-LZIP, a larger amount of the LZIP N-terminal was detected in the nucleus than in the cytoplasm, like the case described above (see FIG. 8B). These results indicate that the Golgi stress by BFA separates and activates the LZIP N-terminal, and the activated LZIP N-terminal moves to the nucleus and binds to the ApoA4 promoter to regulate the expression thereof.

1-3. Change in Expression of ApoA4 by LZIP N-Terminal

In order to directly confirm an effect of the LZIP N-terminal on the regulation of expression of ApoA4, after the LZIP N-terminal was replicated and expressed in a liver cell line, the resulting activity of ApoA4 and the resulting change in expression of ApoA4 mRNA and protein were confirmed. Further, by using primary liver cells of mice, the separation of the LZIP N-terminal by the treatment with BFA and the resulting change in expression of ApoA4 mRNA and protein were again verified. In the following Examples, for the treatment with or expression of the LZIP N-terminal, Flag-LZIP-N (pCMV-3 Tag-1 vector where an LZIP N-terminal sequence in which a Flag epitope (DYKDDDDK) is tagged at the N-terminal is cloned), or Ad-LZIP-N (pShuttle-IRES-hrGFP-2 vector where an LZIP N-terminal sequence in which an HA epitope is tagged at the C-terminal is cloned) was used.

Figure 2A:
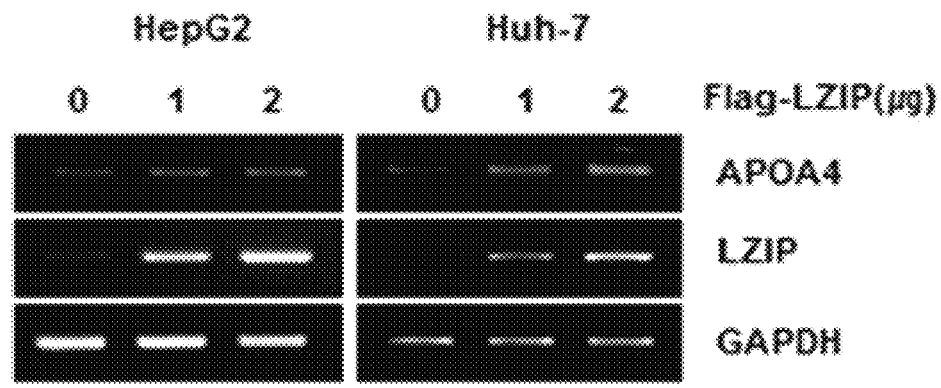
FIG. 2A is a result of confirming a change in expression level of ApoA4 mRNA according to the concentrations (0, 1, and 2 μg) in treatment with a Flag-LZIP.
Figure 2B:
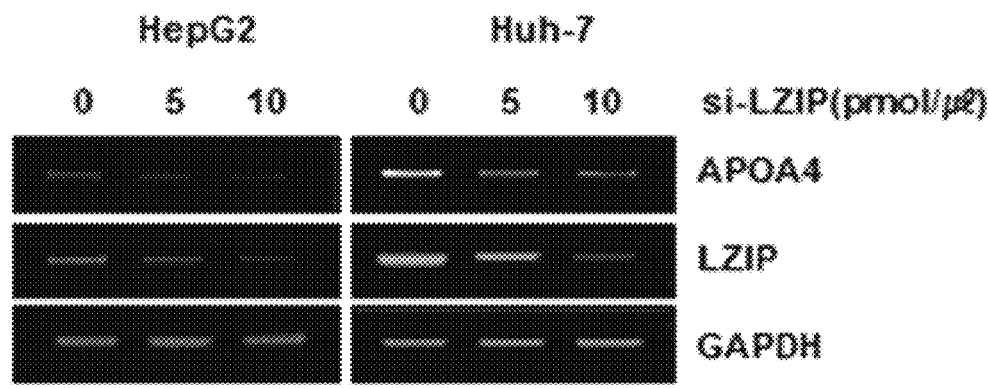
FIG. 2B is a result of confirming a change in expression level of ApoA4 mRNA according to the concentrations (0, 5, and 10 pmol/μl) in treatment with LZIP siRNA.
Figure 3A:
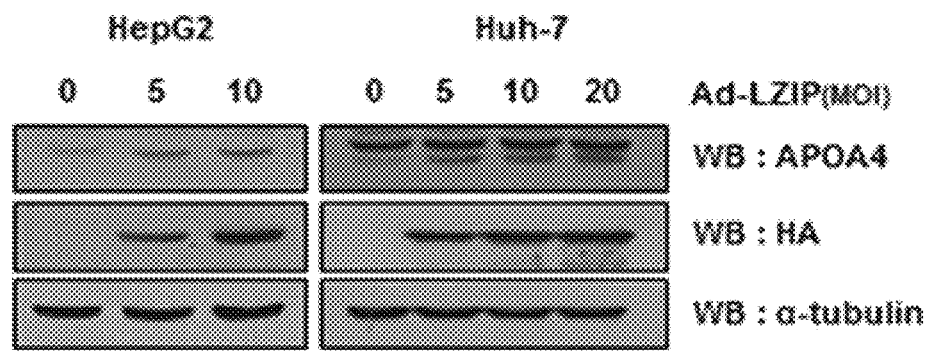
FIG. 3A is a result of confirming a change in expression level of ApoA4 protein according to the concentrations (0, 5, 10, and 20 MOI) in treatment with an Ad-LZIP.
Figure 3B:
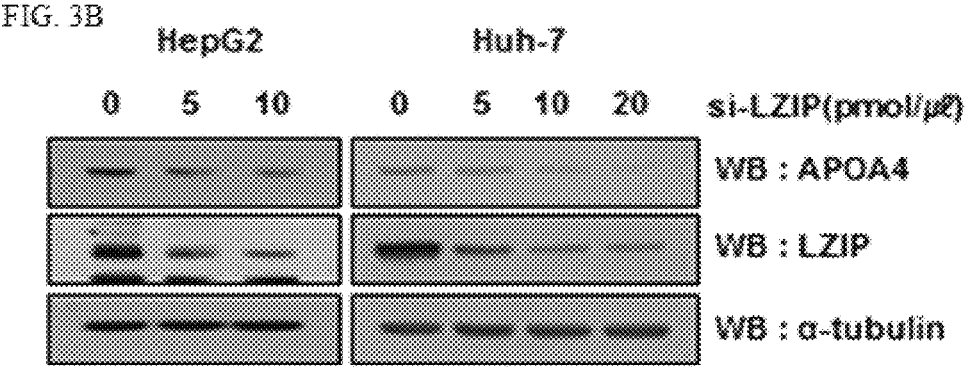
FIG. 3B is a result of confirming a change in expression level of ApoA4 protein according to the concentrations (0, 5, 10, and 20 pmol/μl) in treatment with LZIP siRNA.
Figure 9A:
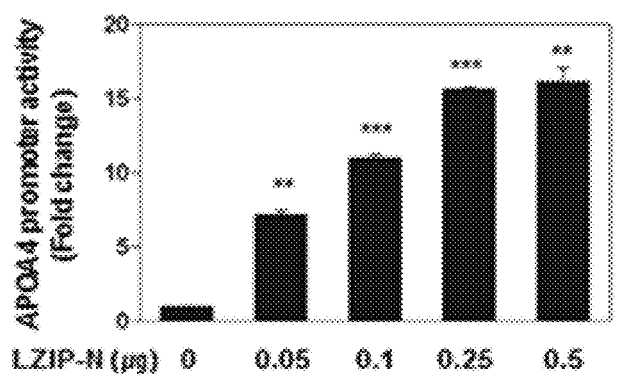
FIG. 9A is a result of measuring the activity of ApoA4 promoter according to the concentrations (0, 0.05, 0.1, and 5 μg) in treatment of an LZIP N-terminal.
Figure 9B:
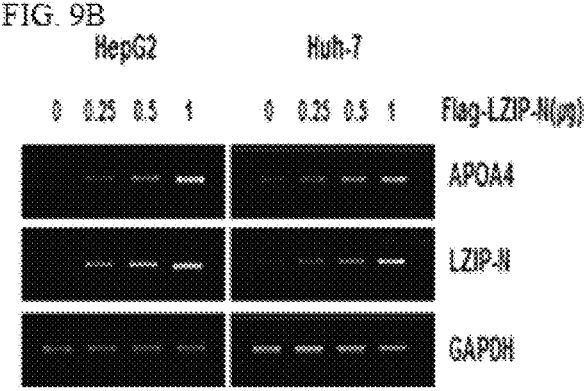
FIG. 9B is a result of confirming a change in expression level of ApoA4 mRNA according to the concentrations (0, 0.25, 0.5, and 1 μg) in treatment of a Flag-LZIP N-terminal.
Figure 9C:
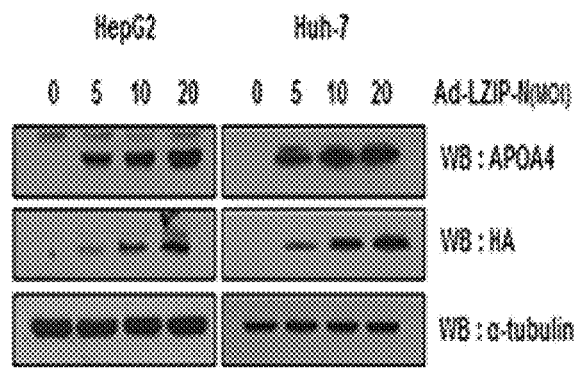
FIG. 9C is a result of confirming a change in expression level of the protein ApoA4 according to the concentrations (0, 5, 10, and 20 MOI) in treatment of an Ad-LZIP N-terminal.
Figure 10A:
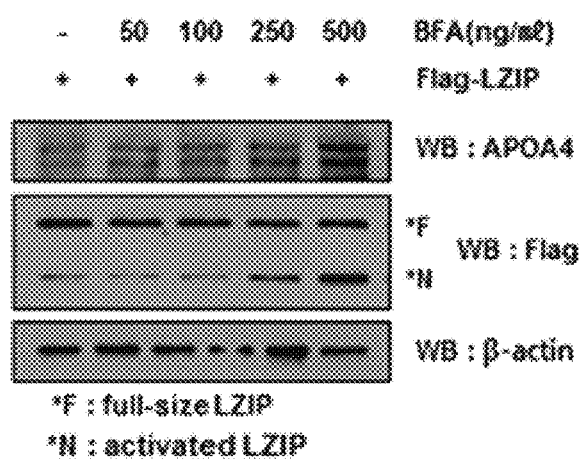
FIG. 10A is a result of confirming separation/production of an LZIP N-terminal protein according to the concentrations (50, 100, 250, and 500 ng/ml) in treatment with BFA.
Figure 10B:
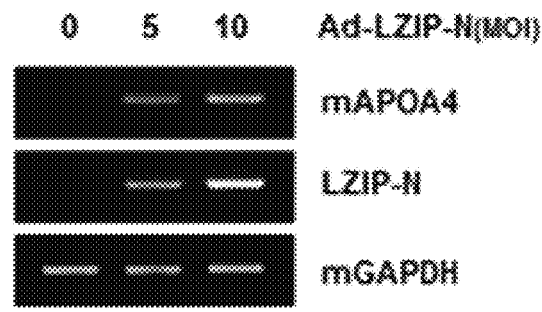
FIG. 10B is a result of confirming a change in expression level of ApoA4 mRNA according to the concentrations (0, 5, and 10 MOI) in treatment of an Ad-LZIP N-terminal.
Figure 10C:
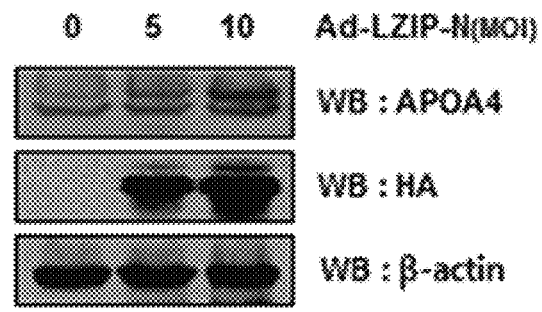
FIG. 10 C is a result of confirming a change in expression level of the protein ApoA4 according to the concentrations (0, 5, and 10 MOI) in treatment of an Ad-LZIP N-terminal.

As a result, as illustrated in FIGS. 9A, 9B and 9C, when the LZIP N-terminal was expressed in a liver cell line, the activity of ApoA4 promoter and the expression of ApoA4 mRNA and protein were increased concentration-dependently, and the effect was a result that the activity and expression were increased much more than the case where cells were treated with a full-length LZIP (see Example 1-1 and FIGS. 1, 2A and 2B). In addition, as illustrated in FIGS. 10A, 10B and 10C, it was confirmed that even in primary liver cells of mice, the LZIP N-terminal separated by the treatment with BFA was increased and the expression of ApoA4 mRNA and protein was increased by the increase in the separated LZIP N-terminal, and it was confirmed again that the expression of ApoA4 in liver cells or tissues was regulated by activation products of the LZIP, and the LZIP N-terminal among the activation products.

Example 2

Stabilization of LZIP N-Terminal by Akt Signaling Mechanism

It is known that the PI3K/Akt signaling system and the PTEN signaling system as a suppressing substance thereof play a very important role in the formation of fatty liver. Thus, in the present example, through an in vitro kinase assay and a GST-pull down assay, it was confirmed whether the LZIP N-terminal of the present invention bound to Akt. Further, based on the result, the amount of the LZIP N-terminal protein by the treatment with an Akt inhibitor and the resulting change in expression of ApoA4 protein were confirmed.

Figure 12A:
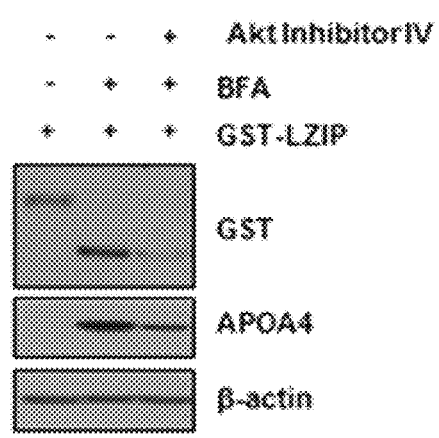
FIG. 12A is a result of confirming a change in expression of the protein ApoA4 according to the treatment with an Akt inhibitor.
Figure 12B:
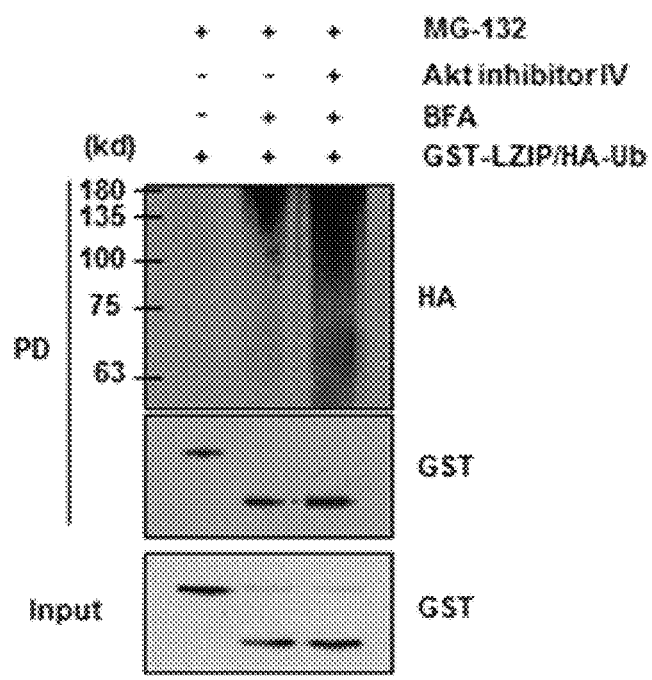
FIG. 12B is a result of confirming the separation of an LZIP N-terminal according to the treatment with an Akt inhibitor.
Figure 12C:
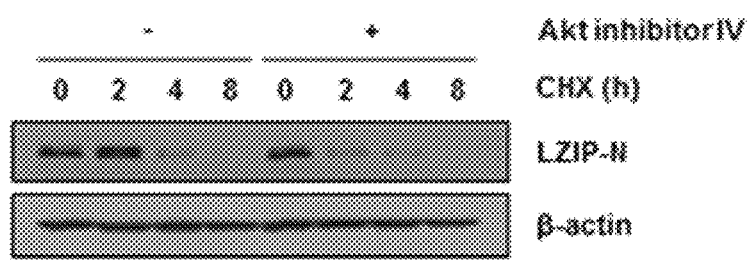
FIG. 12C is a result of confirming a change in stability of an LZIP N-terminal according to the treatment with an Akt inhibitor.

As a result, as illustrated in FIGS. 11A and 11B, the bond between the activated Akt and the LZIP N-terminal could be observed in each experiment. In addition, as illustrated in FIGS. 12A, 12B and 12C, when cells were treated with an Akt inhibitor (Akt inhibitor IV), not only the LZIP N-terminal, but also ApoA4 was remarkably decreased (FIGS. 12A and 12B). Further, as a result of confirming the effect of treatment/non-treatment with the Akt inhibitor on the stability of the LZIP-N while treating cells with cycloheximide in order to suppress the expression of a new protein to be synthesized during the experimental procedure, it was confirmed that when cells were treated with the Akt inhibitor, the stability of the LZIP-N was reduced within a short period of time (FIG. 12C). Accordingly, it could be seen that the change in expression was regulated by interactions between the PI3K/Akt signaling system and the separated LZIP N-terminal.

Example 3

Correlation Between LZIP N-Terminal and Accumulation of Fat in Liver Cells or Tissues In the present example, a correlation between the accumulation of fat in liver tissues, that is, the onset of fatty liver, and the change in expression of ApoA4 by treatment with LZIP N-terminal was intended to be confirmed based on the results of Examples 1 and 2. Specifically, cells were treated with the LZIP N-terminal in combination with oleic acid (OA) causing the accumulation of fat in HepG2 as a human liver cell line or mouse primary liver cells, and then the amount of fat accumulated in liver cells in the combination treatment was compared with the case of the single treatment with oleic acid. Furthermore, the change in expression level of ApoA4 and amount of fat accumulated in liver tissues by the treatment with the LZIP N-terminal for a mouse animal model was confirmed in vivo. Specifically, a virus including the LZIP N-terminal was administered to mice through intravenous injection, and three days later, the expression level of ApoA4, the proportion of triglycerides, and the like were compared and analyzed with those in a control (Ad-GFP) by extracting liver tissues from the mice.

Figure 13A:
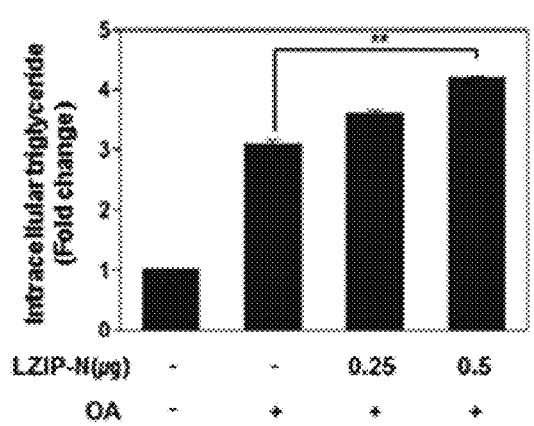
FIG. 13A is a result of confirming an amount of fat accumulated in liver cells by combination administration of oleic acid and an LZIP N-terminal in HepG2 which is a human liver cell line.
Figure 13B:
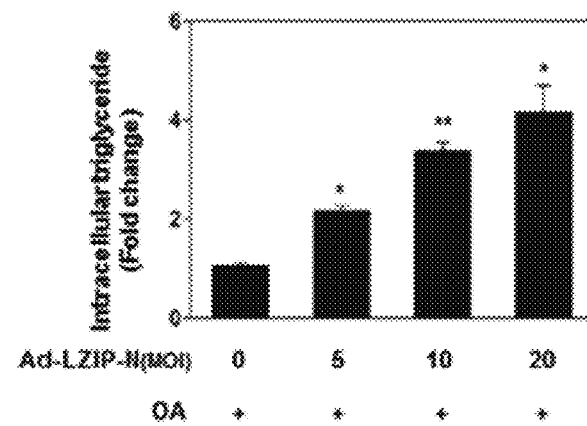
FIG. 13B is a result of confirming an amount of fat accumulated in liver cells by combination administration of oleic acid and an LZIP N-terminal in mouse primary liver cells.
Figure 14:
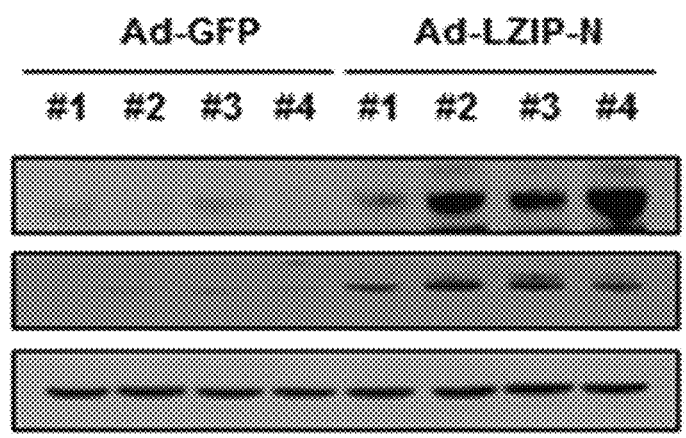
FIG. 14 is a result of confirming a change in expression level of ApoA4 in liver tissue according to the treatment of an LZIP N-terminal using a mouse animal model.
Figure 15A:
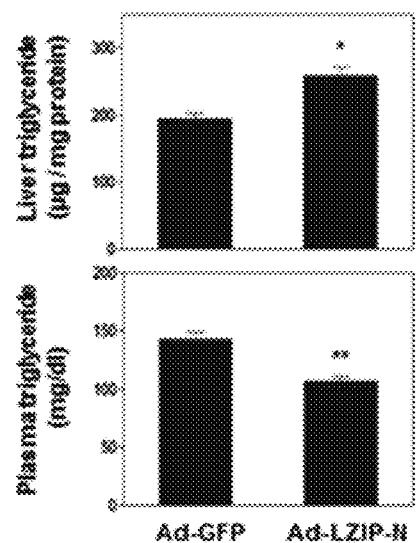
FIG. 15A is a result of confirming a change in amount of triglycerides in liver tissue or plasma according to the treatment of an LZIP N-terminal using a mouse animal model.
Figure 15B:
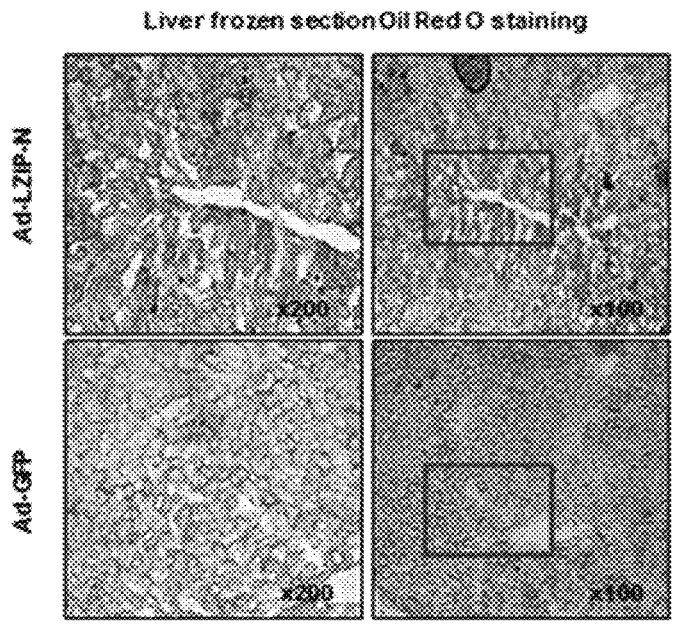
FIG. 15B is a result of confirming triglycerides in liver tissue according to the treatment of an LZIP N-terminal using a mouse animal model by Oil Red O staining.

As a result, as illustrated in FIGS. 13A and 13B, it could be seen that when cells were treated with the LZIP N-terminal in combination with oleic acid, the amount of fat accumulated in liver tissues was increased as compared to the group treated with only oleic acid. This tendency depended on the concentration in treatment with the LZIP N-terminal, and it could be seen that, particularly when mouse primary liver cells were treated with 20 MOI of LZIP N-terminal, the amount of fat that accumulated was increased to about 2.5 times as compared to the group treated with only oleic acid. Further, it was confirmed that in the liver tissues of the mice to which the LZIP N-terminal was administered, as illustrated in FIGS. 14, 15A and 15B, the expression level of ApoA4 was remarkably increased as compared to the control, and the proportion of triglycerides in liver tissue was increased, whereas the proportion of triglycerides in plasma was decreased, and the accumulation of fat in liver tissue, which is the resulting histopathological finding through Oil Red O staining, could be observed. From the results, it could be seen that an increase in ApoA4 in liver tissue caused by the LZIP N-terminal caused the accumulation of fat, which is a major mechanism for the onset of fatty liver.

Example 4

Expression of LZIP and ApoA4 in Various Human Fat Liver Tissues

In Example 3, the effect of accumulating fat in liver cells of mice or liver tissues for mice was confirmed, whereas the present example sought to confirm whether the effect described above could also be observed in humans. Specifically, the expression levels of the LZIP and ApoA4 for fatty liver due to obesity, alcoholic fatty liver, or nonalcoholic fatty liver tissues were compared with those of normal liver tissues.

Figure 16:
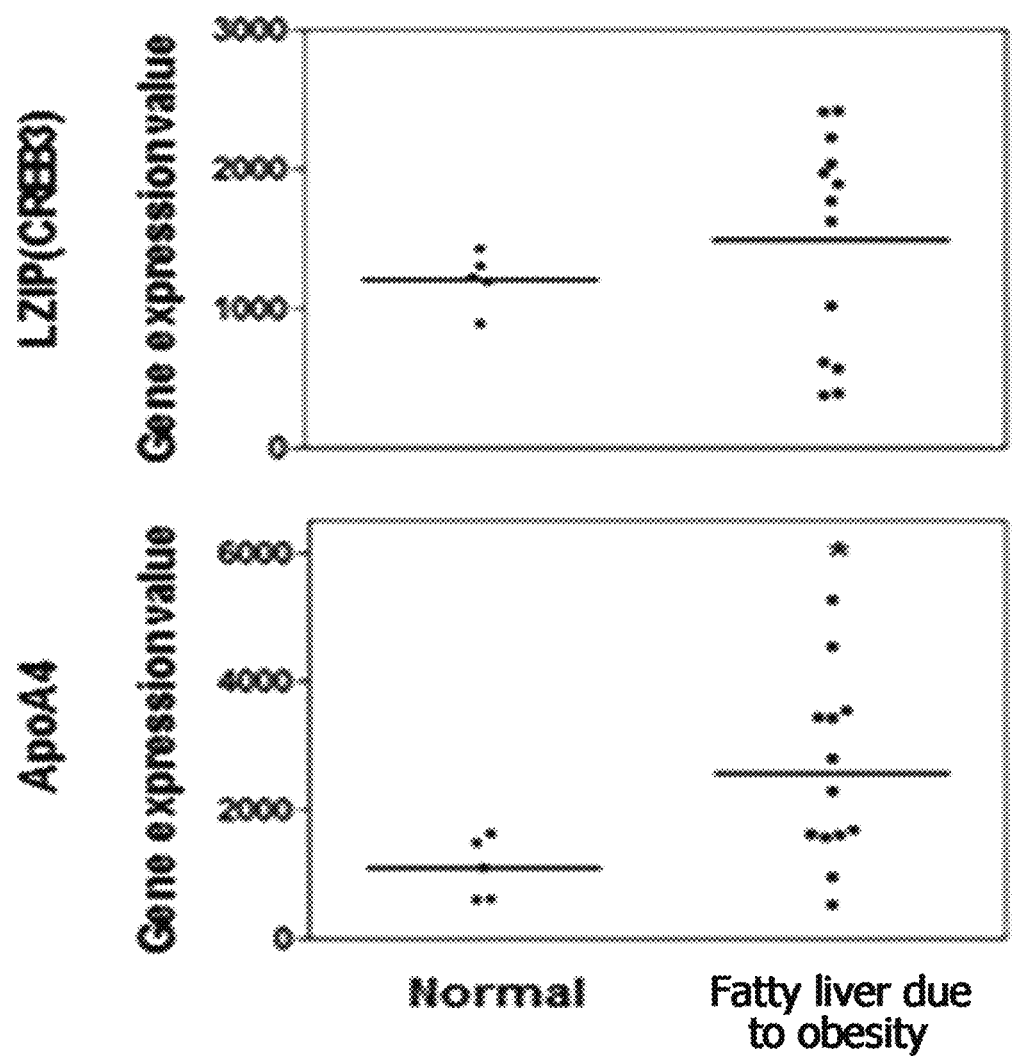
FIG. 16 is a result of comparing the expression of an LZIP or ApoA4 in fatty liver tissue due to obesity with that in normal liver tissue.
Figure 17:
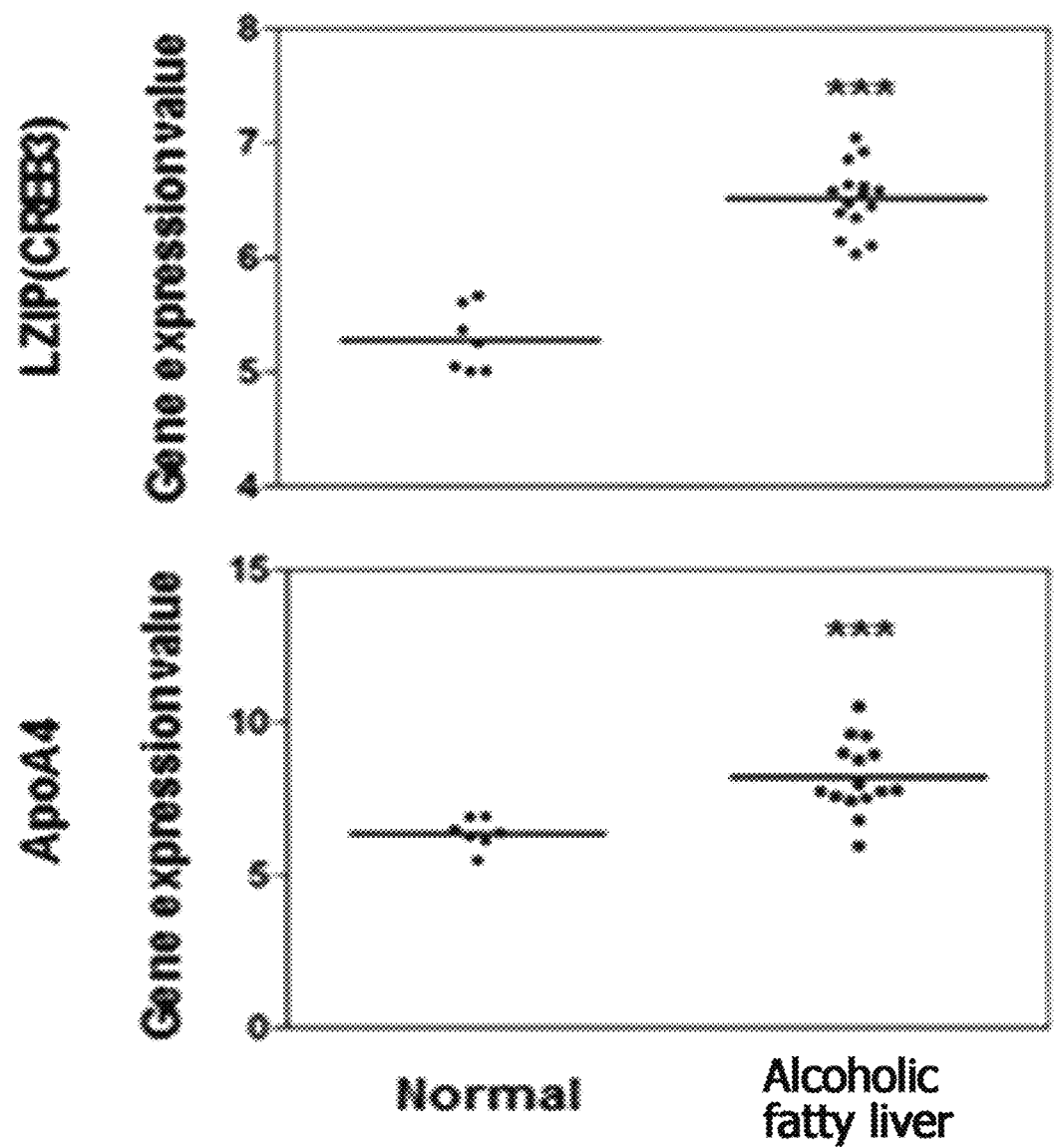
FIG. 17 is a result of comparing the expression of an LZIP or ApoA4 in alcoholic fatty liver tissue with that in normal liver tissue.
Figure 18:
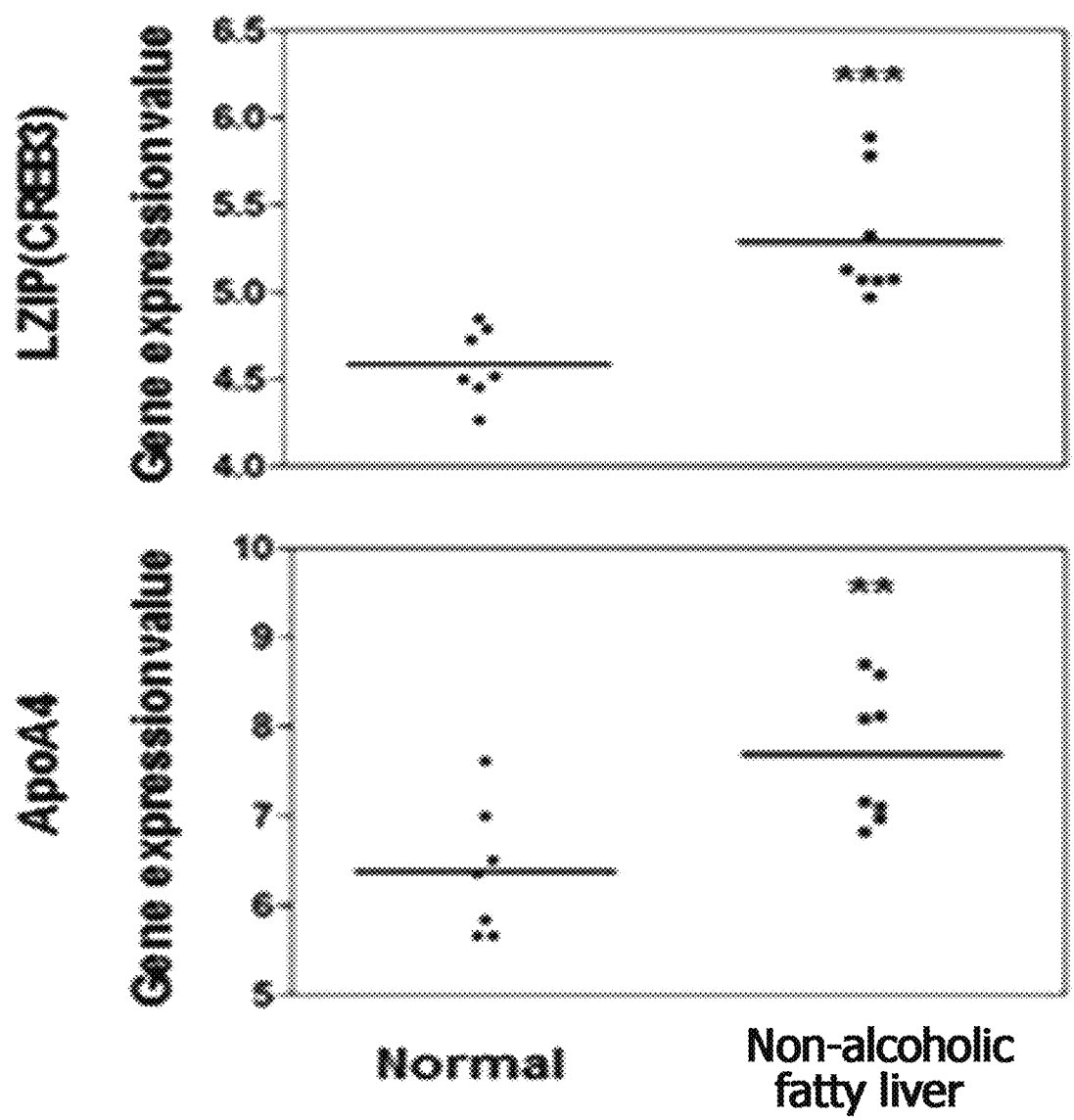
FIG. 18 is a result of comparing the expression of an LZIP or ApoA4 in nonalcoholic fatty liver tissue with that in normal liver tissue.

As a result, as illustrated in FIGS. 16 to 18, it was confirmed that the expression levels of the LZIP and ApoA4 in all of the fatty liver due to obesity, the alcoholic fatty liver, and the nonalcoholic fatty liver were higher than those of normal liver tissues.

When the aforementioned results are put together, it can be seen that the LZIP, particularly the LZIP N-terminal, regulates the expression of ApoA4 protein associated with lipoprotein transport, and accordingly, plays an important role in the accumulation of fat in the liver, and the LZIP N-terminal can be utilized as a core target factor for diagnosis and treatment of fatty liver.

The above description of the present invention is provided for illustrative purposes, and those skilled in the art to which the present invention pertains will understand that the present invention can be easily modified into other specific forms without changing the technical spirit or essential features of the present invention. Therefore, it should be understood that the above-described examples are illustrative only in all aspects and are not restrictive.

The invention claimed is:

1. A method for prevention or treatment of fatty liver, the method comprising:
   a step of administering an inhibitor of expression of a leucine-zipper protein to an individual,
   wherein the inhibitor of expression is an antisense oligonucleotide, siRNA, or shRNA for a gene encoding a fragment consisting of an amino acid sequence of SEQ ID No. 1.

2. A method for prevention or treatment of fatty liver, the method comprising:
   a step of administering an inhibitor of activity of a leucine-zipper protein to an individual,
   wherein the inhibitor of activity is any one selected from the group consisting of an antibody specifically binding to the leucine-zipper protein; an anti sense oligonucleotide, siRNA, or shRNA for a gene encoding a fragment consisting of an amino acid sequence of SEQ ID No. 1; and a phosphatidylinositol-3-kinase (PI3K)/Akt inhibitor.

* * * * *

SEQUENCE LISTING

```
<160> NUMBER OF SEQ ID NOS: 6

<210> SEQ ID NO 1
<211> LENGTH: 219
<212> TYPE: PRT
<213> ORGANISM: Homo sapiens

<400> SEQUENCE: 1

Met Glu Leu Glu Leu Asp Ala Gly Asp Gln Asp Leu Leu Ala Phe Leu
1               5                   10                  15

Leu Glu Glu Ser Gly Asp Leu Gly Thr Ala Pro Asp Glu Ala Val Arg
                20                  25                  30

Ala Pro Leu Asp Trp Ala Leu Pro Leu Ser Glu Val Pro Ser Asp Trp
            35                  40                  45

Glu Val Asp Asp Leu Leu Cys Ser Leu Leu Ser Pro Pro Ala Ser Leu
    50                  55                  60

Asn Ile Leu Ser Ser Ser Asn Pro Cys Leu Val His His Asp His Thr
65                  70                  75                  80

Tyr Ser Leu Pro Arg Glu Thr Val Ser Met Asp Leu Glu Ser Glu Ser
                85                  90                  95

Cys Arg Lys Glu Gly Thr Gln Met Thr Pro Gln His Met Glu Glu Leu
                100                 105                 110

Ala Glu Gln Glu Ile Ala Arg Leu Val Leu Thr Asp Glu Glu Lys Ser
            115                 120                 125

Leu Leu Glu Lys Glu Gly Leu Ile Leu Pro Glu Thr Leu Pro Leu Thr
    130                 135                 140

Lys Thr Glu Glu Gln Ile Leu Lys Arg Val Arg Arg Lys Ile Arg Asn
145                 150                 155                 160

Lys Arg Ser Ala Gln Glu Ser Arg Arg Lys Lys Lys Val Tyr Val Gly
                165                 170                 175

Gly Leu Glu Ser Arg Val Leu Lys Tyr Thr Ala Gln Asn Met Glu Leu
            180                 185                 190

Gln Asn Lys Val Gln Leu Leu Glu Glu Gln Asn Leu Ser Leu Leu Asp
        195                 200                 205

Gln Leu Arg Lys Leu Gln Ala Met Val Ile Glu
    210                 215

<210> SEQ ID NO 2
<211> LENGTH: 657
```

<212> TYPE: DNA
<213> ORGANISM: Homo sapiens

<400> SEQUENCE: 2

```
atggagctgg aattggatgc tggtgaccaa gacctgctgg ccttcctgct agaggaaagt    60
ggagatttgg ggacggcacc cgatgaggcc gtgagggccc cactggactg ggcgctgccg   120
ctttctgagg taccgagcga ctgggaagta gatgatttgc tgtgctccct gctgagtccc   180
ccagcgtcgt tgaacattct cagctcctcc aaccccctgcc ttgtccacca tgaccacacc   240
tactccctcc cacgggaaac tgtctctatg gatctagaga gtgagagctg tagaaaagag   300
gggacccaga tgactccaca gcatatggag gagctggcag agcaggagat tgctaggcta   360
gtactgacag atgaggagaa gagtctattg gagaaggagg ggcttattct gcctgagaca   420
cttcctctca ctaagacaga ggaacaaatt ctgaaacgtg tgcggaggaa gattcgaaat   480
aaaagatctg ctcaagagag ccgcaggaaa agaaggtgt atgttggggg tttagagagc   540
agggtcttga atacacagc ccagaatatg gagcttcaga acaaagtaca gcttctggag   600
gaacagaatt tgtcccttct agatcaactg aggaaactcc aggccatggt gattgag      657
```

<210> SEQ ID NO 3
<211> LENGTH: 372
<212> TYPE: PRT
<213> ORGANISM: Homo sapiens

<400> SEQUENCE: 3

```
Met Glu Leu Glu Leu Asp Ala Gly Asp Gln Asp Leu Leu Ala Phe Leu
1               5                   10                  15

Leu Glu Glu Ser Gly Asp Leu Gly Thr Ala Pro Asp Glu Ala Val Arg
            20                  25                  30

Ala Pro Leu Asp Trp Ala Leu Pro Leu Ser Glu Val Pro Ser Asp Trp
        35                  40                  45

Glu Val Asp Asp Leu Leu Cys Ser Leu Ser Pro Pro Ala Ser Leu
    50                  55                  60

Asn Ile Leu Ser Ser Ser Asn Pro Cys Leu Val His His Asp His Thr
65                  70                  75                  80

Tyr Ser Leu Pro Arg Glu Thr Val Ser Met Asp Leu Glu Ser Glu Ser
                85                  90                  95

Cys Arg Lys Glu Gly Thr Gln Met Thr Pro Gln His Met Glu Glu Leu
            100                 105                 110

Ala Glu Gln Glu Ile Ala Arg Leu Val Leu Thr Asp Glu Glu Lys Ser
        115                 120                 125

Leu Leu Glu Lys Glu Gly Leu Ile Leu Pro Glu Thr Leu Pro Leu Thr
    130                 135                 140

Lys Thr Glu Glu Gln Ile Leu Lys Arg Val Arg Arg Lys Ile Arg Asn
145                 150                 155                 160

Lys Arg Ser Ala Gln Glu Ser Arg Arg Lys Lys Val Tyr Val Gly
                165                 170                 175

Gly Leu Glu Ser Arg Val Leu Lys Tyr Thr Ala Gln Asn Met Glu Leu
            180                 185                 190

Gln Asn Lys Val Gln Leu Leu Glu Glu Gln Asn Leu Ser Leu Leu Asp
        195                 200                 205

Gln Leu Arg Lys Leu Gln Ala Met Val Ile Glu Ile Ser Asn Lys Thr
    210                 215                 220

Ser Ser Ser Ser Thr Cys Ile Leu Val Leu Leu Val Ser Phe Cys Leu
225                 230                 235                 240
```

Leu Leu Val Pro Ala Met Tyr Ser Ser Asp Thr Arg Gly Ser Leu Pro
            245                 250                 255

Ala Glu His Gly Val Leu Ser Arg Gln Leu Arg Ala Leu Pro Ser Glu
        260                 265                 270

Asp Pro Tyr Gln Leu Glu Leu Pro Ala Leu Gln Ser Glu Val Pro Lys
        275                 280                 285

Asp Ser Thr His Gln Trp Leu Asp Gly Ser Asp Cys Val Leu Gln Ala
        290                 295                 300

Pro Gly Asn Thr Ser Cys Leu Leu His Tyr Met Pro Gln Ala Pro Ser
305                 310                 315                 320

Ala Glu Pro Pro Leu Glu Trp Pro Phe Pro Asp Leu Phe Ser Glu Pro
            325                 330                 335

Leu Cys Arg Gly Pro Ile Leu Pro Leu Gln Ala Asn Leu Thr Arg Lys
            340                 345                 350

Gly Gly Trp Leu Pro Thr Gly Ser Pro Ser Val Ile Leu Gln Asp Arg
            355                 360                 365

Tyr Ser Gly Leu
    370

<210> SEQ ID NO 4
<211> LENGTH: 1116
<212> TYPE: DNA
<213> ORGANISM: Homo sapiens

<400> SEQUENCE: 4

```
atggagctgg aattggatgc tggtgaccaa gacctgctgg ccttcctgct agaggaaagt      60
ggagatttgg ggacggcacc cgatgaggcc gtgagggccc cactggactg ggcgctgccg     120
ctttctgagg taccgagcga ctgggaagta gatgatttgc tgtgctccct gctgagtccc     180
ccagcgtcgt tgaacattct cagctcctcc aaccctgcc ttgtccacca tgaccacacc     240 tactcccctcc cacgggaaac tgtctctatg gatctagaga gtgagagctg tagaaaagag     300
gggacccaga tgactccaca gcatatggag gagctggcag agcaggagat tgctaggcta     360
gtactgacag atgaggagaa gagtctattg gagaaggagg ggcttattct gcctgagaca     420
cttcctctca ctaagacaga ggaacaaatt ctgaaacgtg tgcggaggaa gattcgaaat     480
aaaagatctg ctcaagagag ccgcaggaaa aagaaggtgt atgttggggg tttagagagc     540
agggtcttga atacacagc ccagaatatg gagcttcaga caaagtaca gcttctggag     600 gaacagaatt tgtcccttct agatcaactg aggaaactcc aggccatggt gattgagata     660
tcaaacaaaa ccagcagcag cagcacctgc atcttggtcc tactagtctc cttctgcctc     720
ctccttgtac ctgctatgta ctcctctgac acaaggggga gcctgccagc tgagcatgga     780
gtgttgtccc gccagcttcg tgccctcccc agtgaggacc cttaccagct ggagctgcct     840
gccctgcagt cagaagtgcc gaaagacagc acacaccagt ggttggacgg ctcagactgt     900
gtactccagg cccctggcaa cacttcctgc ctgctgcatt acatgcctca ggctcccagt     960
gcagagcctc ccctggagtg gccattccct gacctcttct cagagcctct ctgccgaggt    1020
cccatcctcc ccctgcaggc aaatctcaca aggaagggag atggcttcc tactggtagc    1080 ccctctgtca ttttgcagga cagatactca ggctag                             1116
```

<210> SEQ ID NO 5
<211> LENGTH: 40
<212> TYPE: RNA
<213> ORGANISM: Artificial sequence

```
<220> FEATURE:
<223> OTHER INFORMATION: Synthetic Construct

<400> SEQUENCE: 5
ccagaugacc acagcauuua ugcuguggag ucaucugguu            40

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Asp Tyr Lys Asp Asp Asp Asp Lys
1               5
```